United States Patent [19]

Senior et al.

[11] Patent Number: 5,266,470
[45] Date of Patent: Nov. 30, 1993

[54] COPOLYMER PRODUCTION

[75] Inventors: Peter Senior, Middlesbrough; Stephen H. Collins, Northallerton; Kenneth R. Richardson, Normanby, all of United Kingdom

[73] Assignee: Imperial Chemical Industries PLC, London, England

[21] Appl. No.: 724,517

[22] Filed: Jun. 28, 1991

Related U.S. Application Data

[63] Continuation of Ser. No. 294,892, Jan. 3, 1989, abandoned, which is a continuation of Ser. No. 863,030, May 14, 1986, abandoned.

[30] Foreign Application Priority Data

May 28, 1985 [GB] United Kingdom ............... 8513310

[51] Int. Cl.$^5$ .......................... C12P 7/62; C12P 7/42; C12N 15/00; C12N 1/20
[52] U.S. Cl. ........................ 435/135; 435/172.1; 435/134; 435/170; 435/146; 435/829
[58] Field of Search ................... 435/135, 172.1, 170, 435/134, 142, 143, 146, 829

[56] References Cited

U.S. PATENT DOCUMENTS

| | | | |
|---|---|---|---|
| 4,138,291 | 2/1979 | Lafferty | 435/135 |
| 4,336,334 | 6/1982 | Powell et al. | 435/146 |
| 4,433,053 | 2/1984 | Hughes et al. | 435/135 |
| 4,477,654 | 10/1984 | Holmes et al. | 435/135 |

OTHER PUBLICATIONS

Bergey's Manual, 1984, Williams & Wilkins pp. 367-373.
"The Prokaryotes", ed. Starr et al, Springer-Verlag 1981—p. 882.

Primary Examiner—Irene Marx
Attorney, Agent, or Firm—Cushman, Darby & Cushman

[57] ABSTRACT

Copolymers of poly(beta-hydroxybutyric acid) and poly(beta-hydroxyvaleric acid) are produced by culturing alcohol-utilizing strains of Alcaligenes eutrophus on a carbon source including primary alcohols having an odd number of carbon atoms such as propan-1-ol.

3 Claims, No Drawings

COPOLYMER PRODUCTION

This is a continuation of application Ser. No. 07/294,892, filed on Jan. 3, 1989, which was abandoned upon the filing hereof which is a continuation of Ser. No. 06/863,030, filed May 14, 1986, now abandoned.

The present invention relates to a process of producing copolymers and in particular to a process of producing copolymers of β-hydroxybutyric acid and β-hydroxyvaleric acids. Hereinafter poly β-hydroxybutyric acid is referred to as PHB and poly β-hydroxyvaleric acid is referred to as PHV. Thus the present invention relates to the production of PHB/PHV copolymers.

PHB is a thermoplastic polyester comprising repeat units of the formula:

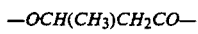

which is accumulated by many micro-organisms, particularly bacteria, for example of the genera Alcaligenes, Athiorhodium, Azotobacter, Bacillus, Nocardia, Pseudomanas, Rhizobium and Spirillim, as an energy reserve material.

Poly 3-hydroxybutyric acid is conveniently prepared by cultivating the micro-organism in an aqueous medium on a suitable substrate, such as a carbohydrate or methanol, as an energy and carbon source. The substrate must, of course, be one that is assimilable by the micro-organism. In order to promote accumulation of the polymer, at least part of the cultivation is preferably conducted under conditions wherein there is a limitation of a nutrient that is essential for growth of the micro-organism but which is not required for polymer accumulation. Examples of suitable processes are described in EP-A-15669 and 46344 and U.S. Pat No. 4,336,334 and 4,433,053.

U.S. Pat. No. 4,477,654 discloses that PHB/PHV copolymers can be made by cultivating certain microorganisms such as *Alcaligenes eutrophus* using certain organic acids, for example propionic acid, or derivatives thereof such as salts or esters, as at least part of the substrate during at least part of the polymer accumulating stage of the cultivation.

PHB/PHV copolymers have a variety of uses in many fields of industry, for example see the article in Chemical Week, 28 August 1985, page 55 and in Manufacturing Chemist, October 1985, page 64.

*Alcaligenes eutrophus* does not normally utilise alcohols such as ethanol, see "The Prokaryotes" Chapter 70, p 882, ed M P Starr et al, published by Springer Verlag (1981). However by mutation and/or selection procedures it is possible to obtain ethanol utilising mutants or variants.

We have found that such ethanol utilising variants are also capable of assimilating other primary alcohols, e.g. propan-1-ol and, when cultivated on a substrate containing a primary alcohol having an odd number of carbon atoms, other than methanol, under conditions conducive to polymer accumulation, accumulate PHB/PHV copolymers.

Accordingly the present invention provides a process for producing a PHB/PHV copolymer comprising cultivating an alcohol-utilising *Alcaligenes eutrophus* strain, that is capable of accumulating poly(β-hydroxybutyrate), under such conditions that the micro-organism accumulates at least 10% by weight of copolymer, wherein, for at least part of the time when the micro-organism is cultivated under the copolymer-accumulating conditions, the substrate comprises at least one primary alcohol, other than methanol, having an odd number of carbon atoms.

Alcohol utilising strains of *Alcaligenes eutrophus* that can be used include strain NCIB 12080 which was deposited with the National Collection of Industrial Bacteria, Aberdeen on 2 May 1985. The latter strain can be obtained from a glucose-utilising strain for example NCIB 11599 (deposited with the National Collection of Industrial Bacteria on 18 August 1980) that does not utilise ethanol, by cultivating the strain, for example NCIB 11599, in continuous culture under oxygen limitation on glucose as substrate and then, transferring to carbon limitation on a substrate containing a mixture of glucose and ethanol with progressive increase in the proportion of ethanols relative to glucose, in the substrate until the substrate was wholly ethanol.

In general ethanol-utilising strains of *Alca igenes eutrophus* are obtained by inducing the enzyme ethanol dehydrogenase. This is conveniently performed by limitation of the oxygen supply. Once the enzyme is induced exposure to ethanol in a continuous culture results in selection of an ethanol-utilising strain. The oxygen availability can be gradually increased to facilitate this selection.

When *Alcaligenes eutrophus* is aerobically cultured on a suitable substrate, i.e. a source of energy and carbon, reproduction occurs until one or more of the essential requirements for reproduction is exhausted. This reproduction of the micro-organism is hereinafter referred to as growth. Upon exhaustion of an essential growth requirement, further growth occurs only to a very limited extent, if at all, but, providing the substrate is not exhausted, a β-hydroxybutyrate polymer may be accumulated by the micro-organism.

With some micro-organisms, even in the absence of a polymer inducing constraint such as a limitation on one or more of the essential growth requirements, polymer may also be accumulated while growth of the micro-organism is taking place: however, except in the case of micro-organisms that produce polymer constitutively, the amount of polymer so accumulated is generally small and typically is less than about 10% by weight of the cells produced. Although there can be a rise of polymer accumulation to about 30% by weight just before complete exhaustion. Thus when grown in batch culture, the micro-organisms that do not produce polymer constitutively, will grow, with little or no polymer accumulation, until one or more of the essential requirements for growth becomes nearly exhausted or exhausted, and then the micro-organism synthesises polymer. In order to produce copolymers it is necessary to use the alcohol containing an odd number of carbon atoms as at least part of the substrate present during the period when copolymer is accumulated.

When the cultivation conditions are such that copolymer is not being accumulated to any significant extent, i.e. where the conditions are such that the amount of copolymer accumulated is less than 10% by weight of the micro-organism cell dry weight, the odd numbered carbon atom alcohol will often be metabolised by the micro-organism by alternative pathways that do not give rise to copolymer: consequently in such cases copolymers will generally not be produced. Metabolism by such other pathways may also occur when using micro-organisms that accumulate copolymer constitutively.

Hence we prefer, even when using constitutive polymer-accumulating micro-organisms, to cause the copolymer to be accumulated by cultivation of the micro-organism under conditions wherein the amount of one or more of the essential requirements for growth, but not polymer accumulation, is limited. Even when cultivating the micro-organism under conditions where there is a restriction of an essential requirement for growth, so that copolymer is accumulated by the micro-organism, some of the alcohol having an odd number of carbon atoms may be metabolised by pathways leading to acetyl CoA or intermediates of the TCA cycle. This enables the micro-organism to synthesise $\beta$-hydroxybutyrate units for incorporation into the copolymer as well as the $\beta$-hydroxyvalerate units, even if the alcohol containing the odd number of carbon atoms is the sole substrate during the polymer accumulation stage.

In order to produce copolymers, the substrate, during at least part of the period copolymer is being accumulated, contains a primary alcohol, other than methanol, containing an odd number of carbon atoms. The alcohol is preferably heptan-1-ol, pentan-1-ol, or particularly, propan-1-ol. Mixtures of such alcohols may be employed. The alcohol, or alcohols, having an odd number of carbon atoms may be used in admixture with another substrate assimilable by the micro-organism for example ethanol or a carbohydrate such as glucose.

In order to obtain a significant proportion of hydroxyvalerate units in the copolymer it is preferred that the amount of combined carbon in the substrate as the alcohol or alcohols having an odd number of carbon atoms is at least 2%, preferably at least 10%, by weight of the total combined carbon in the substrate present during the period when the cultivation conditions are such that copolymer is being accumulated by the micro-organism. Preferably the alcohol of alcohols having an odd number of carbon atoms form at least 25% by weight of the substrate employed during the copolymer accumulation stage.

As indicated above, it is preferred, even when using a micro-organism that produces copolymer constitutively, to conduct the period of cultivation of the micro-organism when copolymer is being accumulated under conditions of limitation of a nutrient required for growth but not for copolymer accumulation.

In addition to the substrate and oxygen (which is generally supplied by injecting air into the aqueous medium in the fermenter), various nutrient salts are required to enable the micro-organism to grow. Thus sources of the following elements in assimilable form, normally as water soluble salts, are generally required: nitrogen, phosphorus, sulphur, potassium, sodium, magnesium, calcium, and iron, together with traces of elements such as manganese, zinc and copper. While it may be possible to induce copolymer accumulation by restricting the supply of oxygen to the fermenter, it is preferred to restrict the amount of one or more of the nutrient salts. The most practical elements to limit are nitrogen, phosphorus, oxygen, or, less preferably, magnesium, sulphur or potassium. Of these it is most preferred to restrict the amount of nitrogen (which is conveniently supplied as an ammonium salt). The amount of assimilable nitrogen required is about 8-15% by weight of the desired weight of cells less accumulated copolymer.

The fermentation is preferably conducted so that the dry weight of the copolymer-containing cells is at least 5 g per liter of aqueous medium. Hence if, for example, it is desired to produce 10 g per liter of polymer-containing cells having a copolymer content of 40% by-weight, the amount of the essential nutrient fed to the fermenter that is used to limit the amount of cell growth must be that required to support the growth of 6 g per liter of cells containing no copolymer: thus, if nitrogen is employed as the growth limiting nutrient, since the nitrogen content of copolymer free bacterial cells is about 8-15% by weight, the amount of assimilable nitrogen required would be between about 0.5 and 0.9 g per liter, e.g. about 0.6 to 1.2 g of ammonium ions per liter.

The fermentation may be conducted under the conditions e.g. pH, temperature, and degree of aeration (unless oxygen is utilised as the limiting nutrient) conventionally used for *Alcalieenes eutrophus* micro-organisms. Likewise the amounts of nutrient salts (other than the growth limiting nutrient whose amount may be determined following the considerations outlined hereinbefore) employed may be those normally used for growth of the micro-organism.

The micro-organism is preferably grown to a certain desired weight by cultivation in the presence of sufficient of the nutrient required for growth that is to be restricted in the copolymer accumulation stage on a readily metabolisable substrate, such as a carbohydrate, and then cultivated under conditions of growth requirement restriction to cause the copolymer accumulation. In some cases the substrate for at least part, and in some cases all, of the growth stage may be the alcohol having an odd number of carbon atoms.

The fermentation may be performed as a batch fermentation in which case copolymer accumulation will occur as the amount of the nutrient that is required for growth but not for copolymer accumulation becomes depleted. Alternatively the fermentation may be conducted as a continuous process wherein aqueous medium containing the bacterial cells is removed, continuously or intermittently, from the fermentation vessel at a rate corresponding to the rate of addition of fresh aqueous medium and substrate thereto. It is preferred that the amount of the nutrient that is restricted that is fed to the fermentation vessel is such that the aqueous medium removed from the vessel contains little or none of that nutrient, and the aqueous medium removed from the vessel is then fed to a second fermentation vessel, operated either in batch or, preferably, continuous fashion wherein copolymer accumulation is caused to take place by continuing the aerobic cultivation with the addition of a fresh quantity of substrate comprising the comonomer component. While additional quantities of substrate and nutrient salts may be added in this further fermentation step, since further growth is generally not desired, little or no further quantity of the nutrient utilised to limit growth should be added. It will however be appreciated that the aqueous medium fed to the further fermenter or fermenters from the first fermenter may contain some residual quantity of the limiting nutrient and/or the addition of a further small quantity thereof may be desireable for efficient operation.

Alternatively the fermentation may be conducted as a single stage continuous process. In order to achieve copolymer accumulation by means of nutrient limitation the residence time of the medium in the fermenter is made sufficiently long to allow the micro-organism to grow and exhaust the limiting nutrient supplied to the fermenter and to allow the micro-organism then to accumulate the copolymer.

In either a batch process, or continuous processes as described above, the alcohol having an odd number of carbon atoms is used as part, or all, of the substrate during the copolymer accumulation stage occurring upon exhaustion of the nutrient required for growth.

The fermentation is preferably conducted so that the amount of accumulated copolymer comprises about 30 to 80% by weight of the bacterial cells.

The copolymer, which generally has a molecular weight above 50,000 (weight average) and has the D(−) configuration, may be extracted from the micro-organism cells by a variety of techniques, for example those described in EP-A-15123.

The invention is illustrated by the following examples.

Description of *Alcaligenes eutrophus* NCIB 12080
Morphology

Growth on CMHO 75% agar, 5 hours at 30° C.
Gram negative mottle rods of approximate size 0.8 μm × 6 μm.
Evidence of intra cellular granules.
No spore formation.
Under a phase contrast microscope occasional subpolar flagella were noted.
Colonial morphology (Lab 8 Nutrient Agar)—the organism is in the form of round, regular, opaque, smooth, white, convex colonies. After 3 days the diameter was about 2 mm.
A pale brown pigmentation developed with increasing age.

Temperature

At 5° C. no growth.
At 37° C. growth.
At 45° C. growth.

| Gram staining (30° C.) | |
|---|---|
| Catalase | + |
| Kovacs Oxidase | + |
| O—F glucose | very weakly oxidative |
| Pyocyanin | − |
| Fluorescence | − |
| L-Arginine CSU | − |
| Betaine CSU | − |
| Glucose CSU | + |
| Lactate CSU | + |
| Acetate CSU | + |
| CSU arabinose | − |
| Meso-inositol | − |
| xylose | − |
| gas glucose | − |
| ONPG | − |
| Arginine Møller | − |
| Lysine Møller | − |
| Ornithine Møller | − |
| $NO_3^-$ to $NO_2^-$ | − |
| $NO_3$ to $N_2$ | + at 37° C. |
| DNA ase | − |
| Gel stab. | − |
| Gel plate | − |
| Casein | − |
| Starch | − |
| Lecithin egg | − |
| Lipase egg | − |
| $NH_3$ | weakly positive |
| Indole | − |
| $H_2S$ | − |
| Tween 80 | + |

| -continued | |
|---|---|
| Gram staining (30° C.) | |
| Urease | + |

No growth exhibited on methanol at 5 or 14 days. Growth exhibited on propan-1-ol at 3 days. Resistant to penicillin G and streptomycin; sensitive to chloramphenicol, tetracycline, polymyxin B and novobiocin (weakly).

EXAMPLE 1

*Alcaligenes eutrophus* variant NCIB 12080 was grown by continuous aerobic cultivation at pH 6.8 and 34° C. in a 5 liter fermenter with a working volume of about 4 liters at a dilution rate (reciprocal of residence time) of 0.1 hr$^{-1}$. The aqueous medium employed had the following composition, per liter of deionised water:

| | mg |
|---|---|
| Phosphorus (as $H_3PO_4$) | 630 |
| Magnesium (as $MgSO_4.7H_2O$) | 80 |
| Potassium (as $K_2SO_4$) | 200 |
| Sodium (as $Na_2SO_4$) | 16 |
| Manganese (as $MnSO_4.4H_3O$) | 1.25 |
| Zinc (as $ZnSO_4.7H_2O$) | 1.15 |
| COpper (as $CuSO_4.5H_2O$) | 0.25 |
| Calcium (as $CaCl_2.2H_2O$) | 36 |

Iron and nitrogen were also continuously supplied, as aqueous solutions containing 11.5 g/l of nitrogen as ammonium hydroxide and 2 g/l ferrous sulphate heptahydrate acidified with sulphuric acid respectively, at such rates that the nitrogen and iron contents of the medium fed to the fermenter were 1040 mg/l and 7 mg/l respectively.

Ethanol and propan-1-ol were supplied at a rate of 12.1 and 12.6 g/l respectively.

pH was controlled at 6.8 by the automatic addition of a 9:1 v/v mixture of 4M potassium hydroxide and 4M sodium hydroxide.

After 5 days steady state fermentation the cell dry weight of the effluent from the fermenter was 16.14 g.l and the cells contained 47% by weight of an PHB/PHV copolymer containing about 20 mol % PHV units and having a melting point of 133° C. (as determined by differential scanning calorimetry).

EXAMPLE 2

Example 1 was repeated with the following changes:

| dilution rate | 0.105 hr$^{-1}$ |
|---|---|
| Nitrogen concentration | 976 mg/l |
| Propanol feed rate | 21.4 g/l |
| Ethanol feed rate | 0 |

After 5 days continuous steady state fermentation the cell dry weight was 12.02 g/l and the cells contained 38% by weight of a polymeric product. The polymeric product contained a higher overall PHV content than the polymer of Example 1 but was a complex product, exhibiting three distinct melting point peaks at 92.4° C., 110° C. and 171° C. This is probably indicative that the polymer is a blend of a β-hydroxybutyrate homopolymer and one or more PHB/PHV copolymers.

EXAMPLE 3

*Alcaligenes eutrophus* NCIB 12080 was grown in a fed-batch technique under aerobic cultivation conditions at pH 6.8 and 34° C. in a 5 liter fermenter. NCIB 12080 culture (80 ml) was inoculated into aqueous medium (3.4 l) of the following composition, per liter of de-ionised water:

|  | mg |
|---|---|
| Phosphorus (as $H_3PO_4$) | 100 |
| Potassium (as $K_2SO_4$) | 250 |
| Magnesium ($MgSO_4.7H_2O$) | 250 |
| Sodium (as $Na_2SO_4$) | 25 |
| Ammonium sulphate (($NH_4)_2SO_4$) | 2000 |
| Trace element solution: | |
| Calcium | 35 |
| Manganese | 1.25 |
| Zinc | 1.15 |
| Copper | 0.25 |
| Iron | 3 |
| Ethanol | 1800 |

The pH was controlled at 6.8 by the automatic addition of 50% vol/vol ammonium hydroxide solution.

After 10.5 hours the culture became carbon limited and a premixed feed of ethanol (335 gl$^{-1}$) and propan-1-ol (52 gl$^{-1}$) was introduced to the fermenter. Overall 620 mls of mixed feed was added to the fermenter over 33 hours so that there was an average rate of addition of ethanol of 2 gl$^{-1}$ hr$^{-1}$.

The final cell dry weight was 33 gl$^{-1}$ and the cells contained 71% by weight of PHB/PHV polymer containing about 10% mol % hydroxyvalerate units. This had a melting point of 158° C. as determined by differential scanning calorimetry.

It is claimed:

1. A process for producing PHB/PHV copolymer comprising cultivating microorganism *Alcaligenes eutrophus* strain NCIB 12080 on an assimilable carbon source under such conditions that the microorganism accumulates copolymer to at least 10% of microorganism dry cell weight and recovering said copolymer from the resulting microorganism, wherein during accumulation of copolymer, the assimilable carbon source comprises at least one primary alcohol selected from the group consisting of propan-1-ol, pentan-1-ol and heptan-1-ol.

2. The process according to claim 1 wherein the primary alcohol provides a carbon content of at least 10% by weight of the total carbon content of said assimilable carbon source present during the copolymer accumulation.

3. The process according to claim 2 wherein the primary alcohol provides a carbon content of at least 25% by weight of the total carbon content of said assimilable carbon source present during the copolymer accumulation.

* * * * *